United States Patent [19]
Barker

[11] Patent Number: 5,818,800
[45] Date of Patent: Oct. 6, 1998

[54] VOICE RECORDING DEVICE HAVING PORTABLE AND LOCAL MODES OF OPERATION

[76] Inventor: Bruce J. Barker, 125 Fifth Ave. Apt. 12D, Pelham, N.Y. 10803

[21] Appl. No.: 478,344

[22] Filed: Jun. 7, 1995

Related U.S. Application Data

[63] Continuation-in-part of Ser. No. 303,128, Sep. 8, 1994, and Ser. No. 226,997, Apr. 13, 1994, Pat. No. 5,548,566, which is a continuation-in-part of Ser. No. 863,950, Apr. 6, 1992, Pat. No. 5,398,220, said Ser. No. 303,128, is a continuation of Ser. No. 29,118, Mar. 10, 1993, abandoned.

[51] Int. Cl.$^6$ .................................................. G11B 19/20
[52] U.S. Cl. ................................................. 369/25; 369/29
[58] Field of Search ................................. 369/25, 27, 29; 395/2.84, 2.4, 164; 345/158, 169; 381/51, 43

[56] References Cited

U.S. PATENT DOCUMENTS

| 3,560,666 | 2/1971 | Bookman | 179/100.11 |
|---|---|---|---|
| 4,245,244 | 1/1981 | Lijewski et al. | 358/111 |
| 4,377,825 | 3/1983 | Kasubuchi et al. | 360/48 |
| 4,426,733 | 1/1984 | Brenig | 455/79 |
| 4,517,424 | 5/1985 | Kroczynski | 200/157 |
| 4,552,360 | 11/1985 | Bromley et al. | 273/85 |
| 4,562,347 | 12/1985 | Hovey et al. | 250/221 |
| 4,605,975 | 8/1986 | Beaman | 360/62 |
| 4,739,128 | 4/1988 | Grisham | 200/6 A |
| 4,754,268 | 6/1988 | Mori | 340/710 |
| 4,758,913 | 7/1988 | Saltzman et al. | 360/72.1 |
| 4,989,253 | 1/1991 | Liang et al. | 381/110 |
| 5,033,077 | 7/1991 | Bergeron et al. | 379/67 |
| 5,036,539 | 7/1991 | Wrench, Jr. et al. | 381/43 |
| 5,045,327 | 9/1991 | Tarlow et al. | 381/51 |
| 5,157,384 | 10/1992 | Greanis et al. | 340/706 |
| 5,161,199 | 11/1992 | David | 381/51 |
| 5,287,119 | 2/1994 | Drumm | 345/158 |
| 5,319,620 | 6/1994 | Hohenbuchler et al. | 369/29 |
| 5,339,095 | 8/1994 | Redford | 345/158 |
| 5,347,630 | 9/1994 | Ishizawa et al. | 395/164 |
| 5,386,494 | 1/1995 | White | 395/2.84 |
| 5,444,768 | 8/1995 | Lemaire et al. | 379/68 |
| 5,477,511 | 12/1995 | Englehardt | 369/25 |

FOREIGN PATENT DOCUMENTS 2161755 1/1986 United Kingdom .
2244546 12/1991 United Kingdom .

OTHER PUBLICATIONS

Mouse With Ears, Anonymous Author, Research Disclosure, Dec., 1991 The document does not specify whether this is the date of publication or some other date such as date of authorship, No. 332, Kenneth Mason Publications Ltd. England.

IBM Independent Series Voice Type User's Guide, Copyright 1991, pp. 28–41 and 60–77.

International Conference on Speech Input/Output, IEEE Conference, A. Edwards, pp. 154–157; Mar. 1986.

Primary Examiner—Tan Dinh

[57] ABSTRACT

An improved voice input peripheral operates in at least two modes, a portable mode (in which the peripheral records a user's voice in the peripheral's memory) and a "local mode" (in which the peripheral downloads the contents of its memory to a computer and is used to control the computer. The peripheral includes a microphone, pointer, a pair of buttons, a bar graph display screen, a loudspeaker and a transmitter. While the user is away from the computer, he places the peripheral in the portable mode. In this mode, the microphone, pointer and pair of buttons allow the user to control the peripheral to store the user's voice in the peripheral's memory. The loudspeaker and bar graph assist the user in locating and listening to desired portions of the recorded voice. When the user returns to the computer, he places the peripheral in the local mode. In this mode, the transmitter downloads the content of the peripheral's memory to the computer and transmits signals to the computer which are representative of the microphone signal, the status of the buttons, and the status of the pointer, to thereby allow the user to operate the computer using the peripheral.

8 Claims, 3 Drawing Sheets

VOICE RECORDING DEVICE HAVING PORTABLE AND LOCAL MODES OF OPERATION

RELATED APPLICATIONS

This is a continuation-in-part of application Ser. No. 08/226,997 filed Apr. 13, 1994, now issued as U.S. Pat. No. 5,548,566 which is a continuation-in-part of U.S. patent application Ser. No. 07/863,950 filed Apr. 6, 1992, which issued as U.S. Pat. No. 5,398,220. U.S. Pat. No. 5,398,220 is hereby incorporated by reference. This is also a continuation-in-part of co-pending application Ser. No. 08/303,128 filed Sep. 8, 1994 still pending which is a continuation of application Ser. No. 08/029,118 filed Mar. 10, 1993 now abandoned.

BACKGROUND OF THE INVENTION

The invention relates generally to data entry into a computer, particularly computers having the ability to store and/or process voice data.

An operator of a computer typically enters data into a computer by typing the data on a keyboard attached to the computer. Some computers also include a microphone which provides the computer with an electrical representation of a user's voice. Such computers may include voice recognition software for converting the electrical representation of the user's voice to text. See for example, U.S. Pat. No. 5,036,539 entitled "Real Time Speech Processing Development System"; and U.S. Pat. No. 5,005,203 entitled "Method Of Recognizing Continuously Spoken Words", both of which are incorporated herein by this reference. Others store the voice for later reproduction by a loudspeaker (e.g., voice mail systems or multimedia computer systems).

The object of the present invention is to provide an improved voice input peripheral. Another object of the present invention is to provide a portable dictation recording peripheral which includes a transmitter for rapidly transmitting an output signal representative of recorded dictation to a receiving device such as a computer.

SUMMARY OF THE INVENTION

The invention relates to an improved voice input peripheral which operates in at least two modes, a portable mode (in which the peripheral records a user's voice in the peripheral's memory) and a "local mode" (in which the peripheral downloads the contents of its memory to a separate device and controls the separate device). (Examples of such separate devices include computers or other sophisticated devices operated by user control, particularly devices which have display screens, graphic user interfaces, and/or voice command capability herein "computers").

In one embodiment, the peripheral includes a microphone, pointer, a pair of buttons, a bar graph display screen, a loudspeaker and a transmitter. While the user is away from his computer, he places the peripheral in the portable mode. In this mode, the microphone, pointer and buttons allow the user to control the peripheral to store the user's voice in the peripheral's memory. The loudspeaker and bar graph assist the user in locating and listening to desired portions of the recorded voice. When the user returns to the computer, he places the peripheral in the local mode. In this mode, the transmitter downloads the content of the peripheral's memory to the computer and transmits signals to the computer which are representative of the microphone signal, the status of the buttons, and the status of the pointer, to thereby allow the user to operate the computer using the peripheral.

Other objects, features and advantages of the invention are apparent from the following description of preferred embodiments taken together with the drawings.

DESCRIPTION OF THE PREFERRED EMBODIMENT

Figure 1:
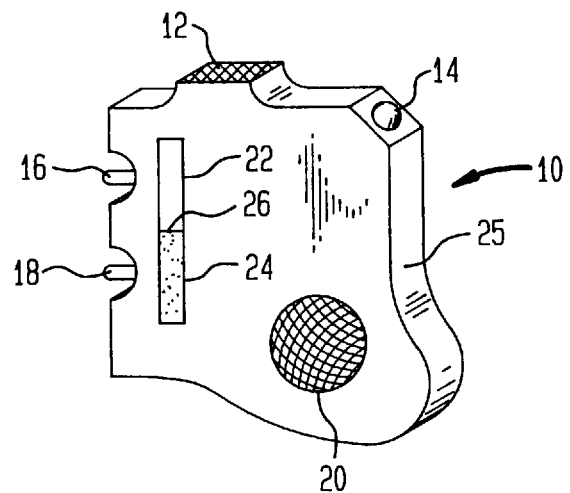
FIGS. 1 and 2 are illustrations of a hand held universal voice input peripheral.

FIG. 1 illustrates a handheld input peripheral 10 according to the invention. The input peripheral includes a microphone 12 for receiving a person's voice; a pointer device 14 (such as a trackball or joystick); a pair of buttons 16,18 (e.g., electromechanical switches, membrane switches or any similar type of transducer known to those skilled in the art); a loudspeaker 20 and a bar graph display 22. The peripheral shown in FIG. 1 is designed for right handed users. The user holds the peripheral with the right side 25 pressed in the palm of his hand (or against the base of his thumb), the pointer 14 positioned beneath the thumb, and the buttons 16,18 positioned beneath his fingers. Thus, the user can easily operate transducers 14, 16, and 18 with his right hand without obstructing the bar graph display 22 or loudspeaker.

The peripheral operates in at least two modes of operation, a "portable mode" (in which the peripheral is used to record a user's voice) and a "local mode" (in which the peripheral is used to control a separate device such as a computer, television or other sophisticated device which allow user control, particularly devices which have display screens, graphic user interfaces, and/or voice command capability).

A. Operation In The Portable Mode

In the "portable mode" the user speaks into the microphone while asserting button 16 to record his voice in an internal memory 64 (FIG. 4) within the peripheral. The bar graph display indicates the status of the internal memory. When the memory is empty, i.e., has no recorded voice, the bar graph is not illuminated. As the peripheral records the user's voice, illuminated portion 24 of bar graph display 22 gradually rises to indicate that memory is being filled with voice. When the memory is full, the illuminated portion reaches the top of the bar graph display, thereby indicating that the peripheral cannot record any further dictation.

To listen to the recording, the user pulls the pointer 14 downward with his thumb. The peripheral responds by gradually moving a cursor 26 from the top of the illuminated portion 24 of the bar graph 22 downward into the body of the illuminated portion until the user releases the pointer. Thus, by moving the cursor and watching the display bar 22, the user selects a location within the recording. For example, if the cursor is in the middle of the illuminated portion, it identifies the middle of the recording.

When the user has moved the cursor to identify a desired location within the recording, he asserts button 18. In response, the peripheral begins to reproduce the recording through the loudspeaker 20 beginning at the selected location. The user can therefore search for a specific location in the stored recording by manipulating the pointer and listening to the playback until he finds desired location.

If the user wishes to record over prior dictation, he selects the desired location using the pointer, asserts button 16 and speaks into the microphone. The peripheral records over the previously stored recording which follows the selected location. If the user desires to insert dictation without destroying the prior recording, the user selects the location for insertion with the pointer, asserts both buttons 16, 18 simultaneously, and begins speaking into the microphone. The peripheral inserts the new recording and updates the bar graph display to indicate that additional memory has been filled.

B. Operation In Local Mode

Figure 2:
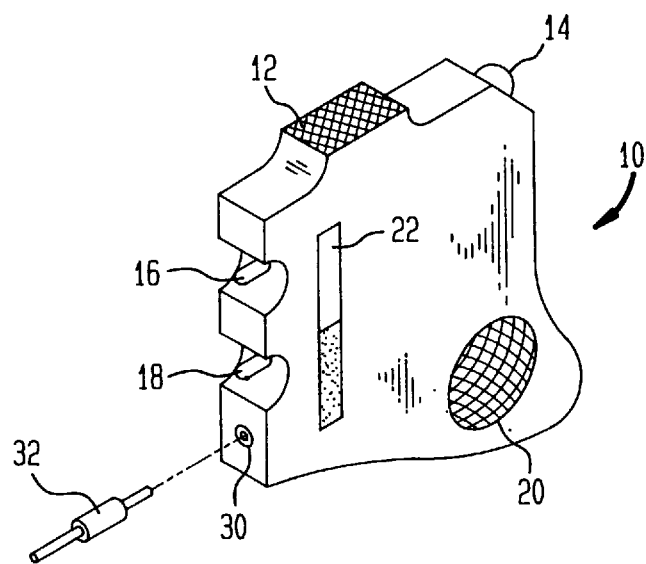
Figure 3:
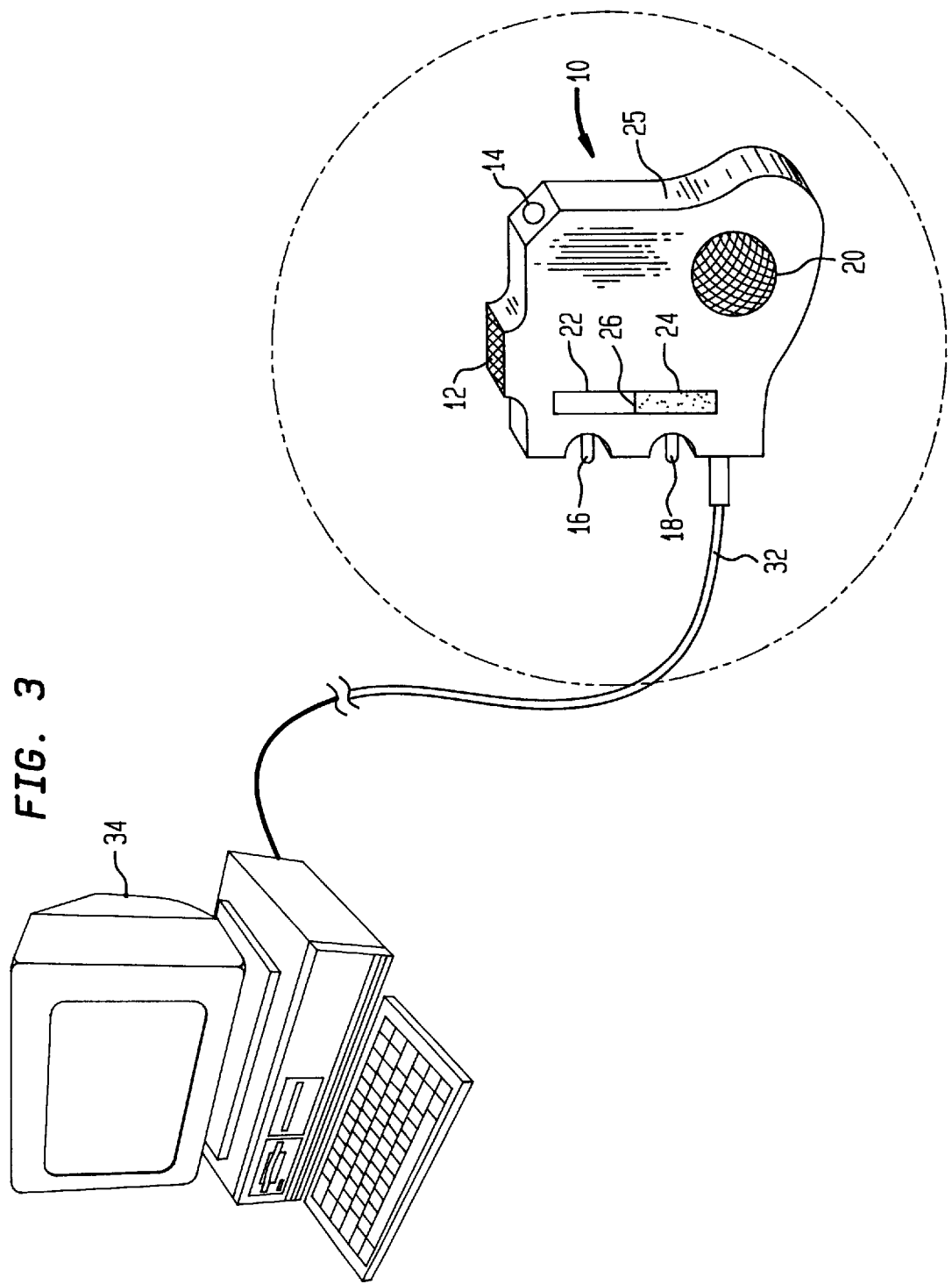
FIG. 3 is an illustration of a hand held universal voice input peripheral connected to a computer.

In the "local mode" of operation, the peripheral operates as an input peripheral to control a computer. As shown in FIGS. 2 and 3, the peripheral includes an output terminal 30 which mates with a cable 32 connected to computer 34. When the peripheral is connected to the computer, the peripheral can rapidly transmit or download any recorded voice stored in the internal memory 64 over the cable 32 to the computer 34. Further, in this mode, signals generated in response to the buttons 16, 18; pointer 14 and microphone 12 are also transmitted over the cable to control the computer 34 as described below. (In alternative embodiments, the peripheral includes a wireless transmitter for transmitting this information to the computer.)

To record dictation directly into the computer's memory, the user asserts the record button 16 and begins speaking into the microphone. Since the peripheral is in local mode, it transmits to the computer a signal which indicates that the record button has been asserted and a microphone signal representative of the user's voice. (The microphone signal is either an analog signal or, in embodiments in which an A/D is housed within the peripheral, a digital signal). In response, the computer begins storing digital samples of the microphone signal in a memory within the computer. To terminate dictation, the user releases the record button 26.

The computer can use the microphone signal for a variety of purposes. For example, if the computer includes speech recognition software, it may analyze the stored samples and prepare therefrom a document containing a textual transcript of the speech. The transcript document is displayed on the computer's display screen for viewing by the user. Alternatively, the computer may analyze the samples to determine if the voice includes spoken commands to be executed by the computer. If the computer includes (or is connected to) a loudspeaker system, it can later reproduce the stored recording through the loudspeaker (e.g., as in a voice mail system or a multimedia computer system).

The peripheral can also be used to navigate the computer's graphic interface using the pointer 14, buttons 16,18; and microphone 12. For example, to modify a document, the user manipulates pointer 14 to thereby move the "cursor" on the computer display screen to the location in the document which requires editing. The pointer is housed in the same handheld chassis which houses the microphone and is conveniently positioned beneath the user's thumb. Accordingly, the user need not release the microphone to operate a separate cursor control mechanism. Rather, he simply manipulates the pointer with his thumb to direct the cursor to the desired location.

Once the cursor is in place, the user can insert new text at the selected location by asserting the record button and speaking into the microphone as described above. In response to the record signal and microphone signals sent by the peripheral, the computer converts the voice to text and inserts the text at the selected location.

The user can also manipulate blocks of text. First, to mark or "select" a block of text, the user positions the cursor to a desired location using the pointer. He then asserts the voice command button 18 and speaks the word "mark" into the microphone. Since the peripheral is in local mode, the peripheral transmits a voice command signal over cable 28 in response to the assertion of button 18 to notify the computer that the microphone signal represents a spoken command. The computer therefore examines the microphone signal to identify the spoken command "mark". (It does not transcribe the word "mark" for insertion in the document).

Upon recognizing the command "mark", the computer notes that the position of the cursor marks the beginning of a block of text. The user then repositions the cursor to a new position, asserts the command button 18 and again speaks the command "mark" to thereby notify the computer that the new cursor location marks the end of the block. After selecting the block of text, the user can verbally instruct the computer to remove the selected text from the document with the voice command "cut". If the user wishes to replace the text at a different location in the document, he repositions the cursor to the desired location and issues the vocal command "paste". In response, the computer inserts the selected text into the document at the cursor position. As demonstrated above, the command button 18 assures that the computer does not confuse commands such as "cut" or "paste" for words to be added to a document.

Since the "cut", "copy", "delete" and "paste" functions may be used frequently in some editing applications, the peripheral may include additional finger actuated buttons, not shown in the figures, which, when asserted, instruct the computer to perform these functions. Similarly, a special button can be added for selecting items from the graphic user interface which are identified by the cursor, or one of buttons 16, 18 can serve this purpose by operating as a selection button when the cursor is in certain fields of the display screen and performing its normal function when the cursor is in other fields of the display screen.

Since the buttons 16, 18 and pointer 14 are housed in the same chassis as the microphone 12, and are conveniently located beneath (or within reach of) one of the user's fingers, the user can dictate text into the computer, move the cursor on the computer's display screen and manipulate the text, all with the same handheld peripheral. Thus, the user need not release the peripheral and move his hands to another input device to perform the above described functions. Further, when he leaves the computer, he can bring the universal voice input peripheral with him for operation in the portable mode discussed above.

C. Internal Structure/Operation

Figure 4:
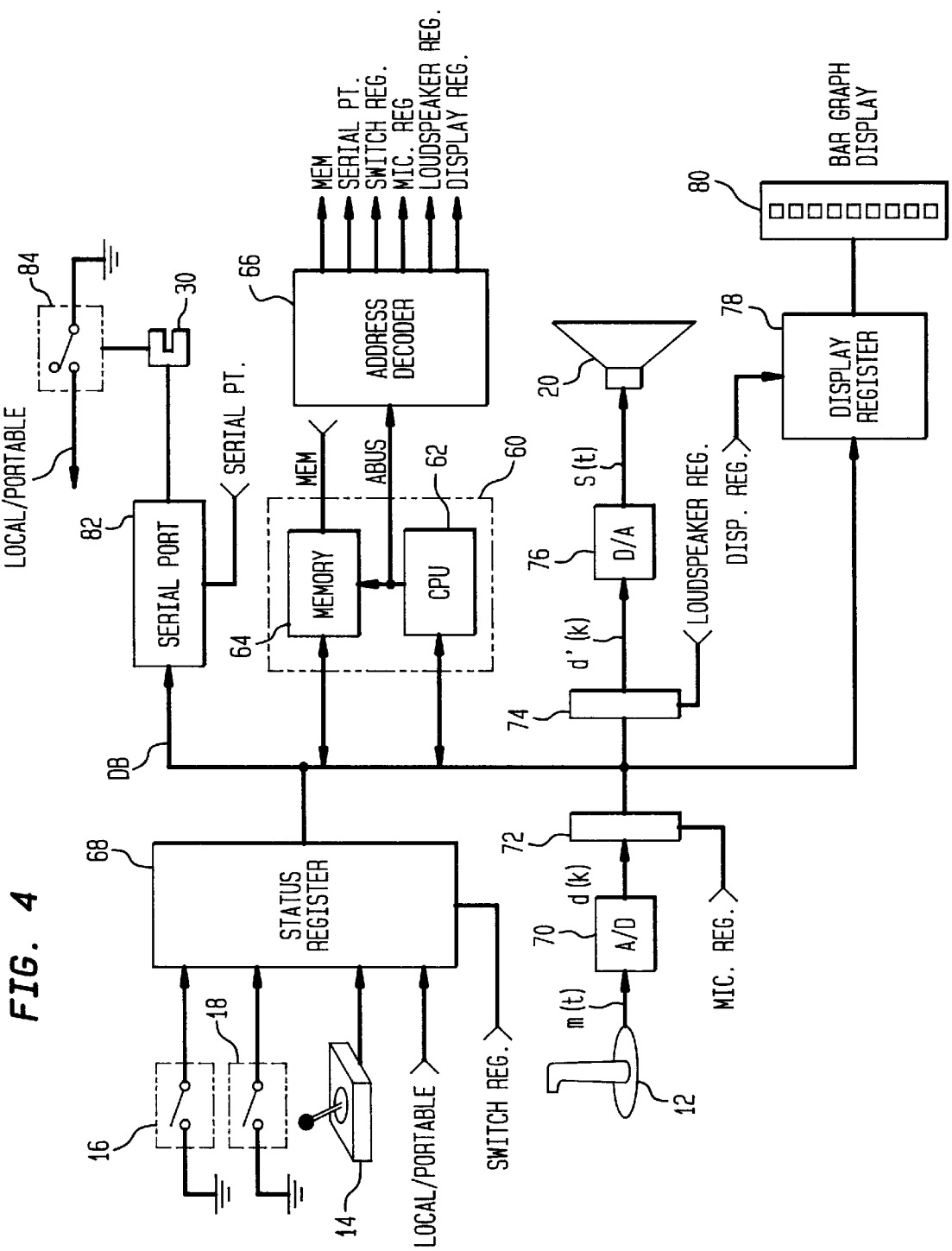
FIG. 4 is a block diagram of the input peripheral depicted in FIGS. 1,2, and 3.

FIG. 4 is a block diagram of the components of a universal voice input peripheral such as depicted in FIGS. 1–3. A controller 60 monitors the status of buttons 16, 18; pointer 14; and local/portable mode switch 84. The status of the local/portable mode switch 84 indicates whether the peripheral is in the local or portable mode. In the example shown, the switch is set to local mode when cable 32 is connected to terminal 30 and to the portable mode when cable 32 is removed from terminal 30.

The controller 60 includes a central processor unit (CPU) 62 and a memory 64. The memory stores a program which is executed by CPU 62 to operate the peripheral. To determine the status of the buttons, pointer and switch, the program instructs CPU 62 to read a status register 68 whose content indicates the status of these components. Based on the status, the program instructs CPU 62 to implement the desired operation such as the operations described in sections A and B above.

1. Operation While Local/Portable Switch is in Portable Mode a. Record

A microphone 12 provides a microphone signal m(t) to a digital to analog converter A/D 70. A/D 70 digitizes the microphone signal to produce a corresponding digital signal d(k). It supplies each sample to a microphone register 72 for temporary storage. While record button 16 is asserted, the CPU 62 reads each sample from the register 72 by reading from an address assigned to the register. A decoder 66 decodes the address and asserts a control signal Mic Reg which instructs register 72 to provide a sample d(k) on a data bus DB. CPU 62 receives the sample d(k) from bus DB and stores it in memory 64.

Toward this end, CPU 62 writes the sample d(k) to an address assigned to a location in memory identified by a cursor/memory pointer. Decoder 66 decodes the address and asserts a MEM control signal instructing memory 64 to load the data from data bus DB into a location identified by the address asserted by CPU 62 on an address bus Abus.

After transferring a sample from register 72 to memory, CPU 62 increments the cursor/memory pointer to the next available address in memory and again reads the Status Register 68 CPU repeats the above steps for each sample d(k) until the record button 16 is de-asserted. While the CPU loads memory with samples d(k) it occasionally updates the bar graph display by writing a command(s) to the display register(or controller) 78 instructing it to raise the height of the illuminated portion of bar graph display by an amount which reflects the amount of memory being filled with samples.

b. Move Cursor

Once CPU 62 detects that the pointer 14 has been moved, it writes a command(s) to the display register(or controller) 78 instructing it to move the location of the cursor displayed by the bar graph display in the direction (and by an amount) indicated by the pointer and makes a corresponding change to the cursor/memory pointer.

c. Play

Once CPU 62 detects that play button 18 is asserted, it begins reading samples of d(k) from memory 64 starting at a location identified by the cursor/memory pointer and writes the samples to a loudspeaker buffer 74 at a rate $R_p$. Buffer 74 provides the samples to an A/D converter 76 which converts the samples to a corresponding analog signal S(t). S(t) drives loudspeaker 20 to reproduce the recorded dictation.

c. Insert

If the CPU detects that both buttons 16,18 are simultaneously asserted, it records samples d(k) in memory at a location identified by the cursor/memory pointer without overwriting previously recorded dictation at and following the location. Using data structures and memory management techniques well known to those skilled in the art, the peripheral effectively inserts the new recording into the prior recording at the location identified by the cursor/memory pointer.

2. Operation While Local/Portable Switch is in Local Mode

Once CPU 62 detects that the local/portable switch is in the local mode, it responds differently than described above. If the record button 16 is asserted it reads samples d(k) from the register 72 as described above and forwards them to serial port 82 which transmits them to the computer. If the pointer is moved, the CPU forwards the pointer signals to serial port 82 for transmission to the computer for use by the computer in controlling the computer's display screen cursor. If button 18 is asserted, the CPU sends a signal to the computer via the serial port 82 instructing the computer to enter a command mode in which it treats any samples d(k) subsequently received from the peripheral as spoken commands. The CPU proceeds to send samples d(k) to the computer via serial port 82 until button 18 is de-asserted. When button 18 is de-asserted, the CPU stops sending samples d(k) and sends a message to the computer indicting that the command mode is terminated.

To download any previously recorded dictation which is stored in memory 64, the user operates the above described pointer, microphone and/or button 18 to interact with the computer's graphic and voice command interfaces to instruct the computer to prepare for receiving the transmission and to store the transmission at a location selected by the user. Once the computer is so instructed, the user asserts both the play and record buttons simultaneously to instruct the CPU 62 to download the stored samples. (In an alternative embodiment, serial port 82 is bidirectional and can receive signals from the computer instructing the CPU 62 to begin download). The CPU 62 responds by reading samples of d(k) from memory 64 and writing them to serial port controller 82 at a relatively rapid rate $R_d$, e.g., faster than the rate $R_p$. The CPU transmits the samples at a rapid rate to allow the user to transfer the recorded dictation at a rate substantially greater than the rate at which the dictation was originally recorded.

D. Additional Embodiments

The peripheral can be designed to operate a plurality of different devices. Such a design would include a mechanism for notifying the peripheral of which of the plurality of devices (e.g., computer, interactive television, video game, telephone etc.) is to be controlled. The peripheral then transmits signals representative of the microphone, buttons and/or pointer to the selected device in a format compatible with the selected device. As another example, the dictation could be processed by the peripheral before transmission to the remote device. In such a peripheral, an additional button may be added which when asserted, notifies CPU 62 that the user's voice represents a spoken command for the peripheral. With this device, the user could select the device to be controlled by asserting the additional command button and speaking the name of the device to be operated, e.g., "television".

While the invention has been described in conjunction with preferred embodiments, it is evident that numerous alternatives, modifications, variations and uses will be apparent to those skilled in the art in light of the foregoing description.

What is claimed is:

1. A portable voice storage peripheral comprising:
   a microphone for providing a microphone signal representative of a user's voice,
   a memory device,
   a position transducer for providing a position signal in response to a user's actuation of said position transducer,
   a controller having a portable mode and a local mode of operation, wherein
      during said portable mode of operation, said controller stores in said memory a memory signal representative of said microphone signal commencing at a location in said memory identified by said position signal, and during said local mode of operation, said controller provides said microphone signal, said memory signal and said position signal to a remote voice processing system for controlling said processing system.

2. The portable voice storage peripheral of claim 1 further comprising:

a chassis, having a handle portion shaped to fit in a user's hand, which supports said microphone to allow the user to hold the microphone near the user's mouth while holding said handle portion, and supports said position transducer within the reach of a finger of said hand grasping said handle portion to allow the user to operate said position transducer with said finger while holding said microphone near the user's mouth.

3. The portable voice storage peripheral of claim 2 wherein said position transducer is positioned within the vicinity of a user's thumb of said hand when said user is holding said handle portion, to allow said user to operate said position transducer with said thumb.

4. The portable voice storage peripheral of claim 2 further comprising:

a display device, supported by said chassis, for displaying a cursor representative of a selected location in said memory, wherein said controller, during said portable mode of operation, instructs said display device to display said cursor at a position identified by said position signal.

5. The portable voice storage peripheral of claim 1 further comprising a record button for providing a data notification signal indicating whether said record button is asserted, and wherein:

during said portable mode, said controller, in response to said data notification signal, stores said memory signal in said memory, and during said local mode of operation, said controller provides a signal to said processing system indicating that said record button is asserted.

6. The portable voice storage peripheral of claim 5 further comprising:

a command button for providing a command notification signal indicating whether said command button is asserted, wherein:

during said portable mode, said controller, in response to said command notification signal, interprets said microphone signal to detect spoken commands, and during said local mode of operation, said controller provides a signal to said processing system indicating that said command button is asserted.

7. The portable voice storage peripheral of claim 2 further comprising a record button supported by said chassis at a position in the vicinity of a user's finger when said user is holding said handle portion, for providing a data notification signal indicating whether said record button is asserted, and wherein:

during said portable mode, said controller, in response to said data notification signal, stores said memory signal in said memory, and during said local mode of operation, said controller provides a signal to said processing system indicating that said record button is asserted.

8. The portable voice storage peripheral of claim 7 further comprising:

a command button supported by said chassis at a position in the vicinity of a user's finger when said user is holding said handle portion, for providing a command notification signal indicating whether said command button is asserted, wherein:

during said portable mode, said controller, in response to said command notification signal, interprets said microphone signal to detect spoken commands, and during said local mode of operation, said controller provides a signal to said processing system indicating that said command button is asserted.

* * * * *